United States Patent [19]
Marcy

[11] Patent Number: 4,915,104
[45] Date of Patent: Apr. 10, 1990

[54] NASAL OXYGEN TUBE SUPPORT AND METHOD

[75] Inventor: Lloyd J. Marcy, Chisago City, Minn.

[73] Assignee: Cynthia L. Vogt, White Bear Lake, Minn.

[21] Appl. No.: 294,779

[22] Filed: Jan. 9, 1989

[51] Int. Cl.⁴ ............................................. A62B 9/04
[52] U.S. Cl. ............................... 128/207.18; 128/912; 128/DIG. 26
[58] Field of Search ............... 128/DIG. 26, 911, 912, 128/207.18, 207.13; 439/451; 24/129 A, 129 R, 131 R; 224/910, 207, 247, 248, 251, 252, 268, 269, 271

[56] References Cited

U.S. PATENT DOCUMENTS

| | | | |
|---|---|---|---|
| 484,335 | 10/1892 | Moss | 224/251 |
| 708,090 | 9/1902 | Stonebraker | 24/131 R |
| 1,263,595 | 4/1918 | Nordstrom et al. | 128/207.13 |
| 1,389,833 | 9/1921 | Kent | 24/129 R |
| 2,084,299 | 6/1937 | Borden | 128/204.13 |
| 2,284,069 | 5/1942 | Robertson | 224/910 |
| 2,574,143 | 11/1951 | Colby | 224/1 |
| 2,589,126 | 3/1952 | Payne | 224/247 |
| 2,618,419 | 11/1952 | Vanish | 224/252 |
| 2,684,875 | 7/1954 | Kircher | 24/129 R |
| 2,973,125 | 2/1961 | Parry | 224/207 |
| 3,802,431 | 4/1974 | Farr | 128/207.18 |
| 3,977,638 | 8/1976 | Woodard | 248/102 |
| 4,167,946 | 9/1979 | Sandstrom | 128/DIG. 26 |
| 4,282,871 | 8/1981 | Chodorow et al. | 128/207.18 |
| 4,331,143 | 5/1982 | Foster | 128/DIG. 26 |
| 4,363,432 | 12/1982 | Warthen | 224/247 |
| 4,437,463 | 3/1984 | Ackerman | 128/DIG. 26 |
| 4,480,639 | 11/1984 | Peterson et al. | 128/207.18 |
| 4,774,946 | 10/1988 | Ackerman et al. | 128/207.18 |

Primary Examiner—Edgar S. Burr
Assistant Examiner—Kimberly L. Asher
Attorney, Agent, or Firm—James V. Harmon

[57] ABSTRACT

A nasal oxygen tube and neck support assembly is described which comprises a pair of nasal oxygen tubes connected at their lower end to a furcator and at their upper ends to a nasal oxygen supply manifold, a clasp connected to the oxygen supply tube and most preferably to the furcator to which the tubes are connected. A sling or lanyard is connected to the clasp to extend around the neck of the patient so that a force pulling downwardly on the oxygen tube will be transmitted through the clasp and sling to the patient's neck rather than to the portion of the oxygen tube that extends to the patient's nose.

8 Claims, 1 Drawing Sheet

U.S. Patent
Apr. 10, 1990
4,915,104
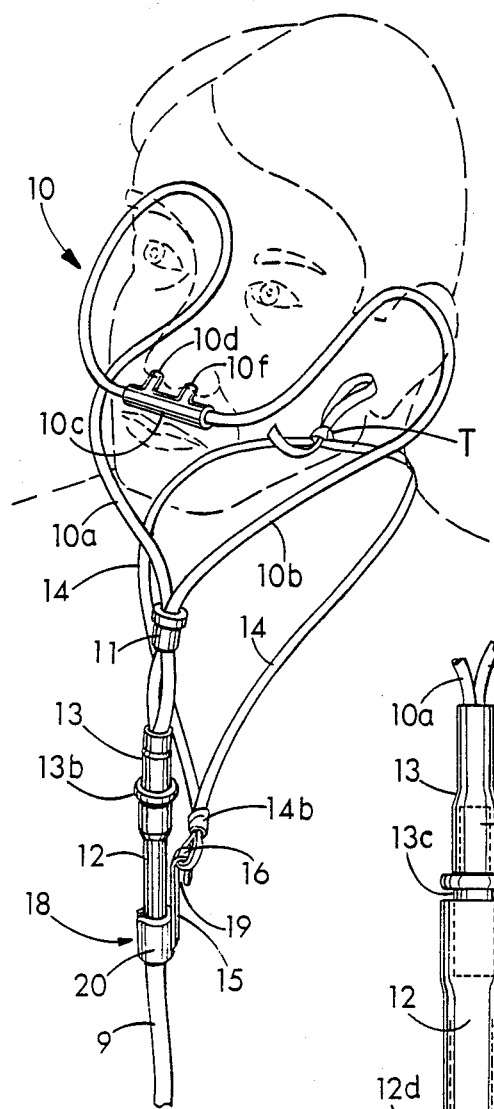
FIG. 1
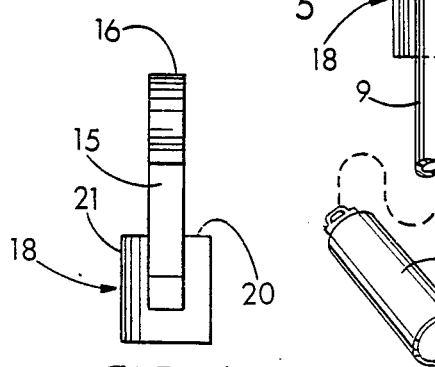
FIG. 4
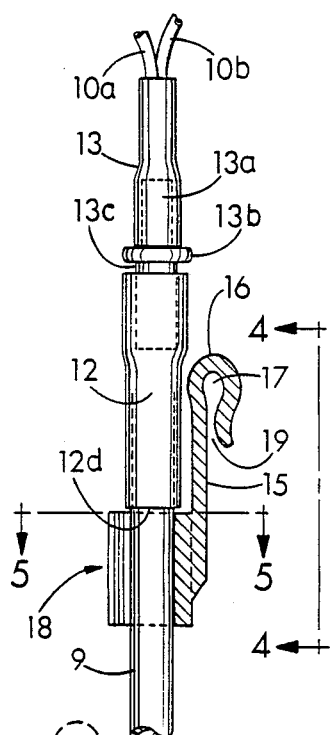
FIG. 2
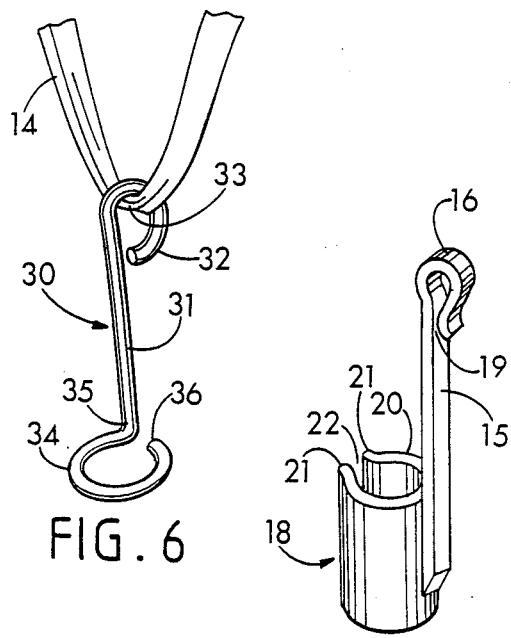
FIG. 6
FIG. 3
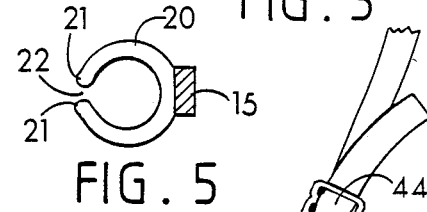
FIG. 5
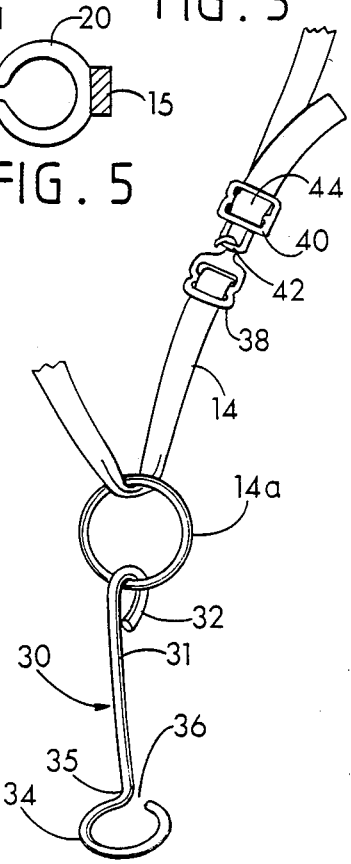
FIG. 7

NASAL OXYGEN TUBE SUPPORT AND METHOD

FIELD OF THE INVENTION

The present invention relates to medical devices and more particularly to a nasal oxygen tube, a support therefor and method of use.

BACKGROUND OF THE INVENTION

Nasal oxygen tubes are in wide use for supplying oxygen to patients with breathing problems. While generally satisfactory in performance, those in current use are sometimes uncomfortable because as the body changes position the head sometimes moves rapidly to one side or toward the rear, pulling on the tube and causing discomfort to the user because the force applied to the tube tends to pull on the user's ears over which the tubes extend. The same thing can happen when changes are being made in the oxygen supply, for example when the oxygen supply tank is being replaced or for any of a variety of other reasons.

If the supply tube is pulled forcefully enough, besides pulling on the ears of the patient, the two smaller oxygen supply tubes that extend over the ears to the nasal manifold can actually be pulled out of the nasal manifold. If the tubes are not pulled out, the nasal manifold can be forced upwardly which tends to push against the nose, causing discomfort for the patient.

SUMMARY OF THE INVENTION

In accordance with the present invention, a nasal oxygen tube and tube support is provided which comprises a furcator having an oxygen supply tube connected thereto for supplying oxygen to the furcator. A pair of nasal oxygen tubes are both connected to the furcator at one end and to a nasal manifold at the other end. The nasal manifold has a pair of outlets to supply oxygen to the nostrils. The oxygen tubes each extend from the furcator upwardly and are adapted to pass behind the ears of the patient and then forwardly to the manifold. A clasp assembly is releasibly connected to the furcator. The furcator preferably rests on an upwardly facing shoulder portion of the clasp. The clasp has an upwardly extending shank and hook portion to which a sling or neck strap formed from flexible material is connected. The sling extends around the neck of the patient to transfer any downward force applied to the oxygen supply tube through the clasp to the patient's neck.

In a preferred form of the invention the clasp includes a C-shaped collar portion which encircles the furcator and/or supply tube and includes a central opening in which the tube is located. The collar has deflectable end portions that enable the C-shaped collar portion of the clasp to be spread apart temporarily so that it can be engaged around the furcator.

These and other more detailed and specific objects of the invention will be apparent in view of the following description and drawings which illustrate by way of example only a few of the various ways in which the present invention can be accomplished within the scope of the appended claims.

THE FIGURES

FIG. 1 is a perspective view of the invention as seen during use.

FIG. 2 is an enlarged side elevational view of the furcator, clasp and associated structure shown in FIG. 1.

FIG. 3 is a perspective view of the clasp.

FIG. 4 is a rear view of the clasp taken on line 4—4 of FIG. 2.

FIG. 5 is a top view of the clasp.

FIG. 6 is a perspective view of another form of clasp in accordance with the invention, and FIG. 7 is a perspective view of the clasp of FIG. 6 showing a different means of connecting the clasp to the sling.

DETAILED DESCRIPTION OF THE INVENTION

As shown particularly in FIGS. 1 and 2, the present invention provides a nasal oxygen tube assembly indicated generally at 10 which includes two oxygen tubes 10a and 10b of sufficient length to extend behind the ears of the patient to a nasal oxygen supply manifold 10c having outlet extensions 10d and 10f that project into the nostrils of the patient during use. The nasal oxygen tubes 10a and 10b pass through an optional slider ring 11 to a furcator having an upper portion 13 and a lower portion 12. The upper portion 13 of the furcator includes a generally cylindrical upright casing 13a which is hollow and into which the nasal oxygen tubes 10a and 10b extend from the top. At the lower end of the casing 13a is a flange 13b. The lower portion 12 of the furcator comprises a tube frictionally fit over the lower end 13c of the casing 13a and connected at its lower end to an oxygen supply tube 9 which is coupled during use to an oxygen tank 8 for the purpose of supplying oxygen through the supply tube 9 to the furcator where it enters the nasal oxygen tubes 10a and 10b passing finally to the manifold 10c and through the outlet ducts 10d and 10f to the nose of the patient.

Two forms of clasps will now be described, one being shown in FIGS. 1–5 and the other in FIGS. 6 and 7.

As shown in FIGS. 1–5, the clasp indicated generally at 18 has a generally C-shaped collar portion 20 which is open at the center and has end portions 21 on either side of a vertically disposed slot 22. The ends 21 are deflectable outwardly so that the sleeve 20 can be engaged around the oxygen supply tube 9 just below the furcator portion 12 so that the upper end of the collar 20 is engaged on the downwardly facing shoulder 12d of the furcator 12.

The clasp 18 also includes an upwardly extending hook member or shank 15 having an outwardly and downwardly curved upper end portion 16 to provide an eyelet 17 with an opening 19 at the bottom to which a lanyard or neck sling 14 is connected. The sling 14 can be formed from any suitable flexible string or strap-like material, a heavy ribbon being preferred, which is tied behind the neck at T in FIG. 1. A grommet 14b can be placed over the lower end of the sling 14 as shown in FIG. 1, if desired, adjacent to the eyelet 17 to help hold the sling 14 in place.

During use, the ends 21 of the collar 20 are spread apart slightly and slipped over the oxygen supply tube 9 as shown in FIGS. 1 and 2, with the shank 15 extending upwardly. The sling or lanyard 14 is then attached to the eyelet 17 and tied as means of the tie T or otherwise fastened around the neck of the patient. As a result, when the oxygen supply tube or the furcator 12, 13 is pulled on or a downward force is applied to it for any reason, this force will be transmitted through the clasp 18 to the sling 14 and to the user's neck, thereby preventing discomfort that would otherwise occur when the force was transmitted to the ears of the patient. The clasp 18 can be formed from any suitable material such as injection molded plastic resin.

Refer now to FIGS. 6 and 7 which illustrate a clasp 30 having a collar portion 34 of circular form positioned to extend horizontally during use with an opening 36 which can be spread apart in the manner of the collar 20 to fit around the oxygen supply tube 9. In this embodiment the clasp 30 is preferably formed from a metal wire or other bendable material, optionally covered with a plastic coating. The clasp 30 has a right angle bend 35 at one side of the opening 36 and extends upwardly therefrom to serve as an upright shank portion 31 terminating in an upper eyelet opening 32 that is connected to the lower portion 33 of sling 14 as shown in FIG. 6. If desired, as shown in FIG. 7, the sling 14 can be connected to the eyelet at the top of shank 31 of the clasp 30 by means of a connecting element such as a ring 14a. FIG. 7 also illustrates other forms of connectors that can be used for the sling 14 such as a pair of fasteners 38, 40 of suitable construction connected or hooked together at 42. The fastener 40 can also be provided with openings through which an end portion of the ribbon that forms the sling 14 passes to make it possible for the patient to easily adjust the length of the sling 14 as conditions of use require.

The nasal oxygen tube assemblies in accordance with the present invention have been used by hospital patients and were found to be much more comfortable than a standard nasal oxygen tube. Moreover, the tube and its associated structure were much less likely to get out of adjustment or be pulled apart. The invention does not get in way, is flexible, conforms to the body, is inexpensive, is rugged in construction and reliable in operation.

Many variations of the present invention within the scope of the appended claims will be apparent to those skilled in art once the principles described herein are understood.

What is claimed is:

1. A nasal oxygen tube assembly having a dual support system comprising, a furcator having an oxygen supply tube connected thereto for supplying oxygen to the furcator, a pair of nasal oxygen tubes connected to the furcator and extending upwardly therefrom, said oxygen tubes being of sufficient length to extend from the furcator to behind the ears of a patient thence forwardly toward the nose, a nasal manifold connected to the oxygen tubes to supply oxygen from the tubes to the nose of a patient, the oxygen tubes being looped over the ears of the patient during use to define a first support means for the assembly which holds the nasal manifold in contact with the patient's nose, and a clasp connected to the furcator, said clasp having a hook and a neck sling or lanyard formed from flexible material connected to the hook and being fastened around the neck of the patient to define a second support means for the assembly that transfers downward forces applied to the furcator and oxygen tube through the clasp to the neck of the patient.

2. The nasal oxygen tube and neck support assembly of claim 1 wherein the clasp is releasably engaged around the oxygen supply tube and includes an upper surface, said furcator has a downwardly facing shoulder and said shoulder is engaged upon the upper surface of the clasp so that a force applied to the furcator in a downward direction will be transmitted via the shoulder to the upper surface of the clasp and thence to the neck sling.

3. The article of claim 1 wherein the clasp has a C-shaped collar portion adapted to encircle the oxygen supply tube adjacent to the furcator and to enclose the oxygen supply tube within an opening at the center thereof, said collar having a slot on one side thereof with deflectable end portions adjacent to the slot to enable the clasp to be spread apart for engagement around the oxygen supply tube.

4. The article of claim 3 wherein the clasp is formed from a plastic resin.

5. The article of claim 3 wherein the clasp is a metal wire having a loop portion defining the collar, said loop being adapted to extend around and encircle the oxygen supply tube, said wire has a right angle bend therein on one side of the loop portion and said wire extends upwardly therefrom to define an upwardly extending shank portion and an eyelet comprising a downwardly bent end portion at the upper end of the shank for fastening the clasp to the neck sling.

6. The article of claim 5 wherein the shank and the loop portion lie in mutually perpendicular planes, the loop in a horizontal plane and the eyelet in a vertical plane, and said eyelet is spaced from the loop by a distance equal to the length of the shank portion of the clasp.

7. A nasal oxygen tube assembly having a dual support system to be used by a patient with breathing difficulties comprising, an oxygen supply tube, a hollow casing connected to the supply tube, a pair of oxygen tubes connected to the casing at one end and having nasal manifold means at the other end, the oxygen tubes being looped over the ears of the patient during use to define a first support means for the assembly which holds the nasal manifold in contact with the patient's nose, a neck strap formed from flexible material for encircling the neck of the patient and a fastener means connected between the casing and the neck strap to define a second support means for the assembly that transfers forces directed downwardly on the casing through the neck strap to the patient's neck.

8. A method of providing dual support for a nasal oxygen tube assembly having an oxygen supply tube to supply oxygen from an oxygen source to a patient, a pair of nasal oxygen tubes connected to the oxygen supply tube at one end and connected at the other end to a nasal manifold to supply oxygen from the tubes to the nose of the patient; said method comprising, maintaining the oxygen tubes sufficiently long to extend from the oxygen supply tube to behind the ears of a patient and thence forwardly proximate to the patient's nose, placing the nasal manifold adjacent the nose of the patient, placing the oxygen tube adjacent the patient's breast, placing one oxygen tube over each ear of the patient during use to define a first support means for the assembly and to hold the nasal manifold in contact with the patient's nose, providing a neck sling, connecting the neck sling to the portion of the nasal oxygen tube assembly adjacent the patient's breast, placing the neck sling around the neck of the patient to define a second support means for the assembly that transfers downward forces applied to the supply tube and the oxygen tubes to the neck of the patient, thereby providing greater safety, stability and comfort for the user.

* * * * *